United States Patent [19]

Middleton

[11] 4,182,760

[45] Jan. 8, 1980

[54] BENZOPHENONE ANTI-OXIMES, DIAZEPIN-N-OXIDES, AND THEIR USE AS PHARMACEUTICAL AGENTS AND AS INTERMEDIATES FOR PHARMACEUTICAL AGENTS

[75] Inventor: William J. Middleton, Chadds Ford, Pa.

[73] Assignee: E. I. Du Pont de Nemours and Company, Wilmington, Del.

[21] Appl. No.: 807,075

[22] Filed: Jun. 16, 1977

[51] Int. Cl.$^2$ .............. C07D 243/24; C07C 103/34; A61K 31/55; A61K 31/165

[52] U.S. Cl. .............................. 424/244; 424/324; 260/239.3 D; 260/562 B

[58] Field of Search ............ 260/239.3 D, 562 B; 424/244, 324

[56] References Cited

U.S. PATENT DOCUMENTS

| | | | |
|---|---|---|---|
| 3,321,467 | 5/1967 | Stempel et al. | 260/562 B |
| 3,453,279 | 7/1969 | Stempel et al. | 260/562 B |
| 3,453,326 | 7/1969 | Stempel et al. | 260/562 B |

FOREIGN PATENT DOCUMENTS

| | | | |
|---|---|---|---|
| 836768 | 6/1976 | Belgium | 260/239.3 D |
| 2460360 | 6/1976 | Fed. Rep. of Germany | 260/239.3 D |

OTHER PUBLICATIONS

Sternbach et al., "Some Aspects of Structure–Activity Relationship in Psychotropic Agents of the 1,4-Benzodiazepine Series", *CSIR*, (1966).

Archer, et al., "The Chemistry of the Benzodiazepines", in *Chemical Reviews*, vol. 68, No. 6, Dec. 1968.

*Primary Examiner*—Natalie Trousof
*Assistant Examiner*—Robert T. Bond

[57] ABSTRACT

N-Fluorohaloacetyl-N-methylaminobenzophenone anti-oxime, the corresponding diazepin-N-oxides, their use as tranquilizers, muscle relaxants and sedatives, and their use as intermediates in the preparation of 3-fluorobenzodiazepines, which are also useful as tranquilizers, muscle relaxants and sedatives.

36 Claims, No Drawings

BENZOPHENONE ANTI-OXIMES, DIAZEPIN-N-OXIDES, AND THEIR USE AS PHARMACEUTICAL AGENTS AND AS INTERMEDIATES FOR PHARMACEUTICAL AGENTS

BACKGROUND OF THE INVENTION

Copending U.S. patent application Ser. No. 687,318, filed May 26, 1976 by Elena M. Bingham and William Joseph Middleton, which is a continuation-in-part of U.S. patent application Ser. No. 597,502, filed July 21, 1975, now abandoned, discloses certain novel 3-fluorobenzodiazepines of the formula:

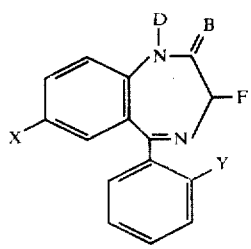

where:

X is Cl, Br, $NO_2$, or $CF_3$;
Y is H, Cl, Br or F;
D is H, hydrocarbyl of 1-4 carbons, $-CH_2CF_3$, $-CONHR$, $-CH_2CH_2NR_2$, or $-CH_2CH_2NR_2 \cdot A$, where R is alkyl of 1-4 carbons and A is a pharmaceutically suitable acid;
B is O; or
B and D together is $=N-N=C(R')-$
where R' is H or $C_1-C_4$ alkyl, and the use of such compounds as tranquilizers, muscle relaxants and sedatives in mammals. In addition, Bingham and Middleton disclose a process for making such compounds by reaction of the corresponding 3-hydroxybenzodiazepine with a dialkylaminosulfur trifluoride as follows:

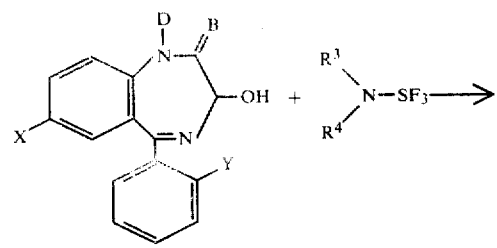

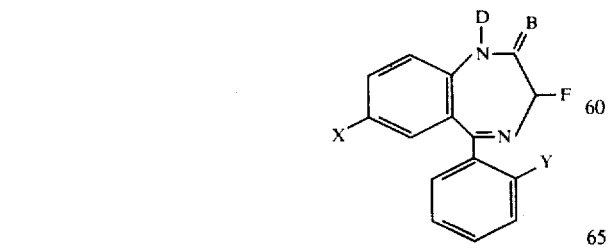

where $R^3$ and $R^4$ are a primary alkyl group of 1-4 carbons or taken together are $-(CH_2)_4-$ or $-(CH_2)_5$.

SUMMARY OF THE PRESENT INVENTION

The present invention relates to an improved process for making such 3-fluorobenzodiazepines, novel intermediates used in the improved process and the further use of such novel intermediates as tranquilizers, muscle relaxants and sedatives in mammals.

More specifically, the present invention relates to:

(A) A new class of tranquilizers and CNS depressants having the general formula II, where X is Cl, Br, $NO_2$ or $CF_3$, Y is H, Br, Cl, or F, and $Z^1$ and $Z^2$ are Cl or Br; and the process for their preparation by the reaction of an anti-oxime of formula I (X and Y as above) with a fluorohaloacetyl halide. The compounds of formula I can be prepared by the process disclosed in U.S. Pat. No. 3,398,139 or by the improved process disclosed in copending U.S. patent application Ser. No. 807,074, filed June 16, 1977 by Arthur J. Elliot and Elena M. Bingham.

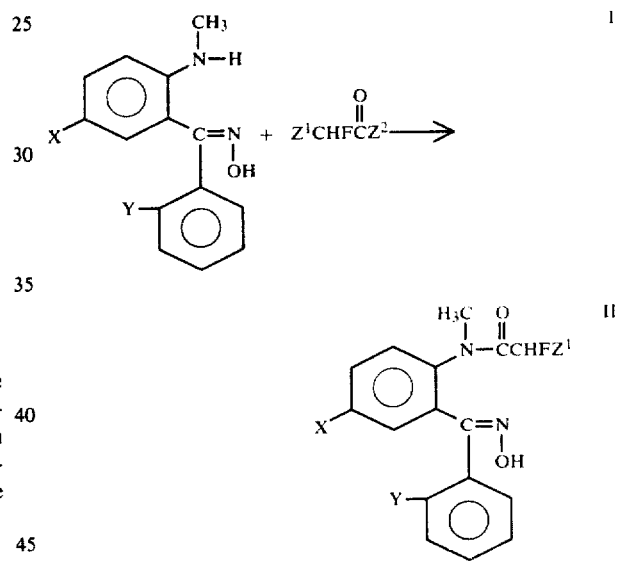

(B) A new class of tranquilizers having the general formula III, where $X = Cl$, Br, $NO_2$ or $CF_3$ and $Y = H$, Br, Cl, or F; and the process for their preparation by treating a compound of structure II with a base.

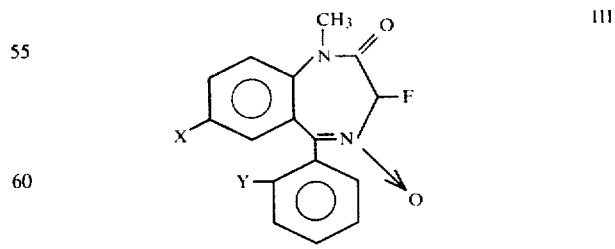

(C) A process for the preparation of tranquilizers of the formula IV, where $X = Br$, Cl, $NO_2$ or $CF_3$ and $Y = H$, Br, Cl, or F, by treating compounds of formula III with a reducing agent.

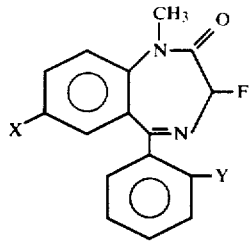

DETAILED DESCRIPTION OF THE INVENTION

Preferred Compounds

Compounds preferred for their activity are those of formulae II and III where X is chlorine or bromine. More preferred compounds are those where X is chlorine or bromine and Y is hydrogen, chlorine or fluorine. Most preferred compounds are those compounds where X is chlorine or bromine and Y is hydrogen or fluorine.

Specifically preferred are the following compounds:
5-chloro-2-(N-methyl-N-chlorofluoroacetamido)benzophenone anti-oxime; and
7-chloro-3-fluoro-1,3-dihydro-1-methyl-5-phenyl-2H-1,4-benzodiazepin-2-one 4-oxide.

Process Conditions (A) Fluoroacetamidobenzophenone anti-oximes of Formula II can be prepared by contacting a solution of a benzophenone anti-oxime of Formula I in an inert solvent with a fluorohaloacetyl halide in either the presence or absence of a suitable base. Inert solvents suitable for use include $CH_2Cl_2$, $CHCl_3$, chlorobenzene, benzene, toluene, and other hydrocarbons or chlorohydrocarbons, diethyl ether, tetrahydrofuran, ethylene glycol dimethyl ether, and other ether solvents, acetonitrile, acetone, and other solvents that are inert to both of the reactants. Although the presence of a base in the reaction mixture is not necessary, the addition of up to one equivalent of a basic material facilitates the reaction and eliminates the tendency of the oximes to isomerize. Bases suitable for use include aqueous solutions of inorganic bases such as NaOH, KOH, $Na_2CO_3$, $K_2CO$, $NaHCO_3$, and $KHCO_3$, and organic tertiary amines such as triethylamine and pyridine, and suspensions of solid inorganic bases such as $NaHCO_3$.

The temperature at which the reaction is conducted is not critical, but it should be below about 100° to prevent isomerization of the oximes and must be above the melting point of the solid so that mixing can be accomplished.

Fluorohaloacetyl halides suitable for use in this reaction include CHFClCOCl, CHFClCOBr, CHFBrCOCl and CHFBrCOBr.

The product of the reaction can be isolated and purified by conventional means, such as recrystallization or column chromatography. If some isomerization does occur during the reaction, or if the starting material is composed of a mixture of syn and anti-oximes, the desired product anti-oxime of Formula II can be separated from its syn-isomer by fractional recrystallization.

(B) 3-Fluorobenzodiazepine oxides of Formula III can be prepared by treating a solution of a fluorohaloacetamidobenzophenone anti-oxime of Formula II with an alkali metal hydroxide. The reaction can be accomplished by mixing a solution of II in a water-immiscible inert solvent, such as $CH_2Cl_2$, $CHCl_3$, chlorobenzene, benzene, toluene, and other hydrocarbon or chlorohydrocarbon solvents, or diethyl ether, with an aqueous solution of NaOH or KOH. Alternately, a solution of II in a water-miscible solvent such as ethyleneglycol dimethyl ether, dioxane, tetrahydrofuran, ethanol, or methanol can be mixed with an aqueous or alcoholic solution of NaOH or KOH. The temperature is not critical, but it is most conveniently carried out from 0° to 25°, although temperatures of up to 80° are operable. The product 3-fluorobenzodiazepine oxides can be isolated from the reaction mixture by conventional means.

Alternately, the 3-fluorobenzodiazepine oxides of Formula III can be prepared in one step from the reaction of benzophenone anti-oximes of Formula I with a fluorohaloacetyl halide in the presence of an alkali metal hydroxide, without isolation of the intermediate fluorohaloacetamidobenzophenone anti-oxime (III).

(C) 3-Fluorobenzodiazepines of Formula IV can be prepared by the reduction of 3-fluorobenzodiazepine 4-oxides (III) with selected mild reducing agents. Suitable reducing agents include, but are not limited to, phosphines of the general formula PR'R''R''', where R', R'' and R''' can be alike or different and include alkoxy, aryloxy, alkyl, aryl, and halo (some specific examples are $P(OCH_3)_3$, $P(OC_2H_5)_3$, $P(butyl)_3$, $PCl_3$, and $PCl_2OCH_3$), and elemental hydrogen in the presence of a suitable catalyst such as finely divided Pt or Pd. The most preferred reducing agent is trimethyl phosphite, since the by-product trimethyl phosphate is water soluble and can be removed from the product 3-fluorobenzodiazepine by washing with water. The phosphines containing halogen bonded to phosphorous are not preferred since hard-to-remove chlorine-containing products are produced as impurities.

An inert solvent for the reduction is usually advantageous, but is not necessary if the reducing agent itself is a liquid.

The reduction is best accomplished at a relatively low temperature to avoid over reduction (loss of fluorine). Ambient temperature (about 20°–25° C.) is preferred, but temperatures from 0° C. to 50° are operable.

The product 3-fluorobenzodiazepine can be isolated from the reaction mixture by evaporation of the solvent and recrystallization of the residue.

The following examples further illustrate how to make the compounds of the present invention and how to conduct the process of the present invention to prepare the 3-fluorobenzodiazepines disclosed by Bingham and Middleton. Parts are by weight and temperatures are in degrees Centigrade unless otherwise specified.

EXAMPLE 1

5-Chloro-2-(N-methyl-N-chlorofluoroacetamido)benzophenone anti-Oxime

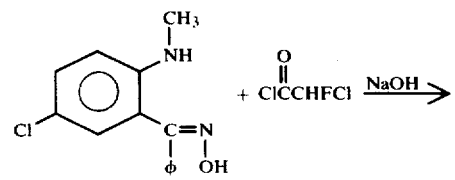

-continued

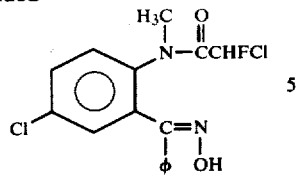

A vigorously stirred mixture of a solution of 104.3 g (0.4 mole) of 5-chloro-2-methylaminobenzophenone anti-oxime in 2 l. of ether and 500 ml of water was cooled to 5°, and (A) 500 ml of 1 N sodium hydroxide and (B) 65.47 g (0.5 mole) of chlorofluoroacetyl chloride made up to 500 ml with ether were added at the same rate over 30 min. from separate dropping funnels. The temperature was maintained at 5° during the additions. The reaction mixture was stirred for an additional 2 hr at 5° to 0°, and then the cold reaction mixture was filtered. The solid collected on the filter was washed with four 50-ml portions of cold ether to remove the slight yellow color. There was obtained 84.93 g of 5-chloro-2-(N-methyl-N-chlorofluoroacetamido)benzophenone anti-oxime as an ether solvate. This product was dried under vacuum at 80° to give 76.35 g (54% yield) of unsolvated material: mp 144°–146°; $^1$H nmr (DMSO-$d_6$) δ 2.68 and 2.96 ppm (for CH$_3$), 6.10 ppm (main doublet, J=49 Hz, for CHF), 7.2–7.7 ppm (aromatic hydrogen) and 11.83 ppm (NOH); $^{19}$F nmr (DMSO-$d_6$) δ −144.6 ppm (d, J=49 Hz, 70%), −138.1 ppm (d, J=49 Hz, 15%) and −145.1 ppm (d, J=49 Hz, 14%) with impurity of 7-chloro-3-fluoro-1,3-dihydro-1-methyl-5-phenyl-2H-1,4-benzodiazepin-2-one 4-oxide at δ −176.8 ppm (d, J=45 Hz).

Anal. Calcd for C$_{16}$H$_{13}$Cl$_2$FN$_2$O$_3$: C, 54.10; H, 3.69; F, 5.35; N, 7.89. Found: C, 53.97; H, 3.90; F, 5.15; N, 7.91.

The ether wash and filtrate were combined, the organic layer was separated, dried over 50 g of magnesium sulfate, and evaporated to dryness under reduced pressure. The residue was suspended in 50 ml of ether, stirred for 5 min., and then cooled. The undissolved material was collected on a filter and washed with three 30-ml portions of cold ether to remove most of the yellow color. There was obtained 49.8 g solvated product, which gave after drying in vacuum at 80°, 44.77 g (32%) of unsolvated 5-chloro-2-(N-methyl-N-chlorofluoroacetamido)benzophenone anti-oxime as a second crop. The total yield of product was 121.12 g, or 85% yield.

EXAMPLE 2

5-Chloro-2-(N-methyl-N-chlorofluoroacetamido)benzophenone anti-Oxime

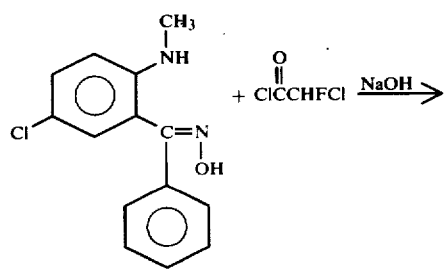

-continued

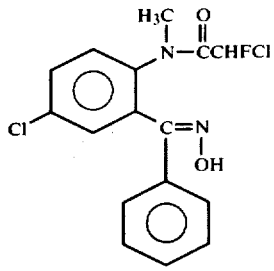

A solution of 15.64 g (0.06 mole) of 5-chloro-2-methylaminobenzophenone anti-oxime in 250 ml of toluene containing 80 ml of water was cooled to 5°, and (A) 75 ml of 1 N sodium hydroxide and (B) 9.82 g (0.075 mole) of chlorofluoroacetyl chloride made up to 75 ml of toluene were added at the same rate over 20 min. from separate dropping funnels. The reaction mixture was stirred for 2 hr. The solid that formed was collected on a filter, washed with water, and dried in air. There was obtained 11.96 g (50%) of 5-chloro-2-(N-methyl-N-chlorofluoroacetamido)benzophenone anti-oxime solvated with 0.5 equivalent of toluene, mp 123°–125°.

Anal. Calcd for (C$_{16}$H$_{13}$Cl$_2$FN$_2$O$_2$)$_2$·C$_7$H$_8$: C, 58.37; H, 4.27; F, 4.73; N, 6.98. Found: C, 58.03; H, 4.42; F, 4.75; N, 6.78.

EXAMPLE 3

Part A, N-(2-Benzoyl-4-chlorophenyl)formamide

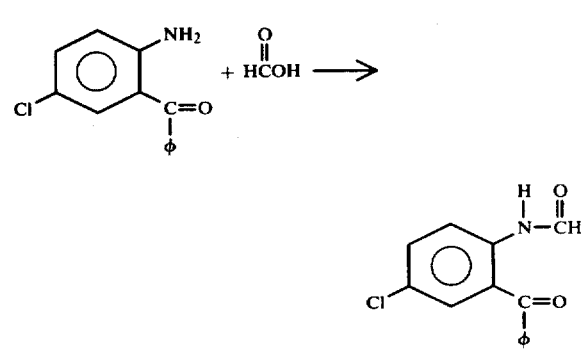

A mixture of 100 g (0.43 mole) of 2-amino-5-chlorobenzophenone and 500 g formic acid was refluxed for 1 hr, and then cooled and poured into 1 l. of ice water. The solid that precipitated was collected on a filter, washed with water, dried in air, and recrystallized from heptane-benzene to give 103.5 g (93%) of the formamide as colorless crystals, mp 89°–91°.

Part B, N-Methyl-N-(2-benzoyl-4-chlorophenyl)formamide

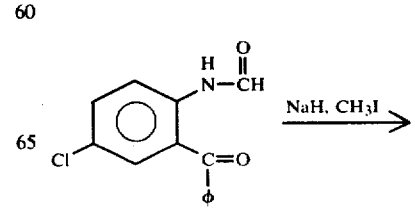

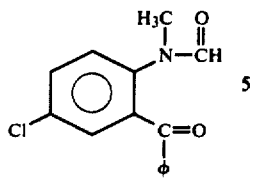

Sodium hydride (0.8 mole, 38.4 g of 50% in mineral oil) was added to a solution of 197.4 g (0.76 mole) of N-(2-benzoyl-4-chlorophenyl)formamide in 800 ml dimethylformamide. When the evolution of hydrogen ceasedm 184 g of methyl iodide was added dropwise at such a rate that the temperature of the reaction mixture slowly rose to 70°. The reaction mixture was stirred for 90 min., and then poured into 2 l. of water. The aqueous mixture was extracted four times with 300 ml portions of methylene chloride, and the combined extracts were washed with water, dried (MgSO$_4$) and evaporated to dryness under reduced pressure. The residue was recrystallized from methanol to give 145.4 g (70% yield) of the N-methylformamide as colorless crystals: mp 93.5°–94.5°; $^1$H nmr (CDCl$_3$) showed two methyl peaks at δ 3.00 and 3.28 ppm (ratio 75:25) and $^1$H nmr (DMSO-d$_6$) showed two methyl peaks at δ 2.94 and 3.23 ppm (ratio 70:30).

Anal. Calcd for C$_{15}$H$_{12}$ClNO$_2$: C, 65.82; H, 4.42; N, 5.12. Found: C, 65.65; H, 4.52; N, 5.11.

Part C, 5-Chloro-2-(methylamino)benzophenone Oxime (Mixture of syn and anti Isomers)

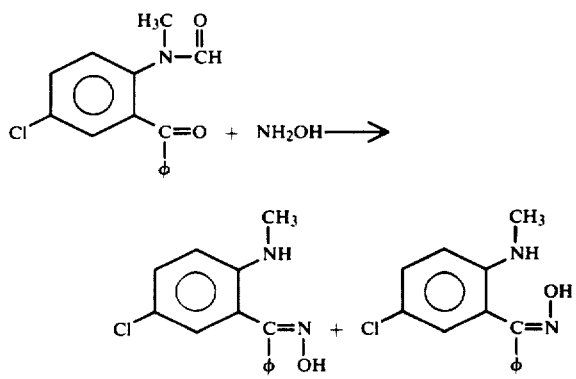

A mixture of 4.0 g (0.1 mole) of powdered sodium hydroxide, 13.9 g (0.2 mole) of hydroxylamine hydrochloride, and 27.4 g (0.1 mole) of N-methyl-N-(2-benzoyl-4-chlorophenyl)formamide in 200 ml of ethanol was refluxed for 3 days. About one-half of the ethanol was distilled off and the reaction mixture was poured into 500 ml of water and then extracted with three 100-ml portions of methylene chloride. The extracts were combined, washed with water, dried (MgSO$_4$) and evaporated to dryness under reduced pressure to give 26 g (100%) of a light yellow glass: $^1$H nmr (DMSO-d$_6$) partial: δ 2.74 ppm (d, J=5 Hz) and δ 2.94 ppm (d, J=5) for CH$_3$ split by NH; δ 11.26 ppm (45%) and 11.53 ppm (55%) for =NOH (on addition of D$_2$O, the splitting of the methyl peaks is lost).

Part D, 5-Chloro-2-(N-Methyl-N-chlorofluoroacetamido)benzophenone Oximes

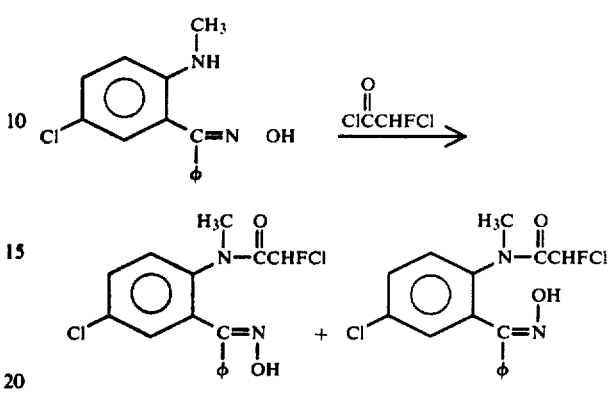

A solution of 26 g (0.1 mole) of 5-chloro-2-(methylamino)benzophenone oxime (mixture of isomers) in 200 ml of ethanol-free chloroform was stirred at room temperature and 14.4 g (0.11 mole) of chlorofluoroacetyl chloride was added dropwise. The reaction mixture warmed spontaneously to 33°. The mixture was stirred for 2 hr, treated to reflux for one hr, and then evaporated to dryness under reduced pressure to give 35.1 g of a light yellow glass. $^{19}$F and $^1$H nmr indicated this product contained a mixture of isomers.

A 15-g sample of this glass was stirred with 150 ml glyme until most of the sample dissolved. The undissolved portion was filtered off and recrystallized from ethanol to give 1.0 g of colorless crystals: mp 240°–243°.

The glyme filtrate was concentrated to one-half its volume by evaporation under reduced pressure, and allowed to remain at room temperature for 3 days. The crystals that formed were collected on a filter and recrystallized from isopropanol to give 6.2 g of 5-chloro-2-(N-methyl-N-chlorofluoroacetamido)benzophenone syn-oxime as colorless crystals: mp 193°–194°; $^{19}$F nmr (DMSO-d$_6$) δ −136.6 ppm (d, J=49 Hz), −144.7 ppm (d, J=49 Hz) and −145.8 ppm (d, J=49 Hz); $^1$H nmr, partial (DMSO-d$_6$) δ 2.80 ppm (s, largest CH$_3$) 6.40 ppm (d, J=49 Hz, largest CHFCl), 12.07 ppm (=N—OH); $^{13}$C nmr, partial (DMSO-d$_6$) δ 36.5 ppm (N-CH$_3$), 163.0 ppm (d, J$_{CF}$=26.5 Hz, C=O), 89.7 ppm (J$_{CF}$=247.1 Hz, —CHFCl), 152.0 ppm (C=NOH).

Anal. Calcd for C$_{16}$H$_{13}$Cl$_2$FN$_2$O$_2$: C, 54.10; H, 3.69; F, 5.35; N, 7.89. Found: C, 54.34; H, 4.00; F, 5.30; N, 7.70.

The filtrate from the isopropyl alcohol recrystallizations was combined with the remaining glyme solution, and this mixture was evaporated to dryness under reduced pressure. After remaining at room temperature for 3 days, this residue became semi-crystalline. This residue was fractionally recrystallized from benzene to give 4.7 g of 5-chloro-2-(N-methyl-N-chlorofluoroacetamido)benzophenone anti-oxime, mp 121°–153°; $^{19}$F nmr (DMSO-d$_6$): δ −144.3 ppm (d, J=50 Hz) and −146.0 ppm (d, J=49 Hz); ratio 2:1.

Anal. Calcd for C$_{16}$H$_{13}$Cl$_2$FN$_2$O$_2$: C, 54.10;H, 3.69; F, 5.35; N, 7.89. Found: C, 54.39; H, 3.98; F, 5.33; N, 7.90.

EXAMPLE 4

Part A.

7-Chloro-3-fluoro-1,3-dihydro-1-methyl-5-phenyl-2H-1,4-benzodiazepin-2-one 4-Oxide

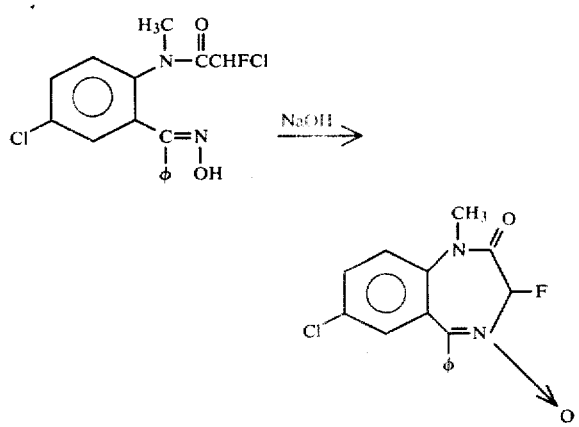

A 2.14-g (6 mmole) sample of 5-chloro-2-(N-methyl-N-chlorofluoroacetamido)benzophenone anti-oxime was added to a stirred solution of 6 ml of 2 N sodium hydroxide in 40 ml glyme cooled to 5°. The reaction mixture was stirred for 30 min. at 5°, and then 20 ml of cold water was added. The reaction mixture was neutralized with 10% hydrochloric acid, and the precipitated solid was collected on a filter, washed with water, recrystallized from methyl ethyl ketone, and dried under vacuum at 100° to give 1.43 g (75%) of 7-chloro-3-fluoro-1,3-dihydro-1-methyl-5-phenyl-2H-1,4-benzodiazepin-2-one oxide as colorless crystals; mp 167°–169°; $^{19}F$ nmr (DMSO-d$_6$) δ −176.9 ppm (d, J=45 Hz); $^1H$ nmr (DMSO-d$_6$) δ 3.48 ppm (s, 3H), 6.39 ppm (d, J=45 Hz, 1H), 7.08 ppm (m, 1H) and 7.6 ppm (m, 7H); ir (KBr) 5.83μ (C=O) and 8.40μ (N→O); $^{13}C$ nmr (DMSO-d$_6$), partial, δ 35.0 ppm (N-CH$_3$), 161.4 ppm (d, $J_{CF}$=26.5 Hz, C=O), 93.8 ppm (d, $J_{CF}$=215 Hz, CHF) and 137.0 ppm (d, $J_{CF}$ 4.4 HZ, C=N).

Part B,

8-Chloro-3-fluoro-1,3-dihydro-1-methyl-6-phenyl-2H-4,1,5-benzoxadiazocin-2-one

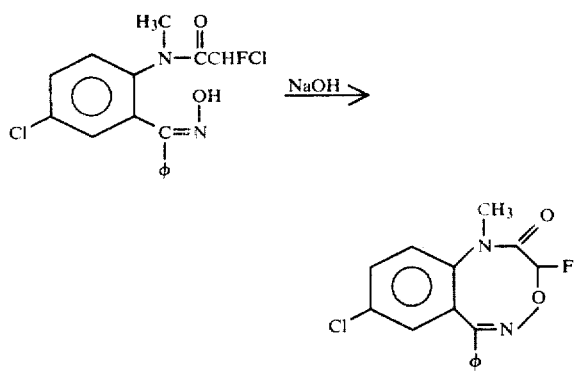

A 2.14-g (6 mmole) sample of 5-chloro-2-(N-methyl-N-chlorofluoroacetamido)benzophenone oxime (syn-isomer, mp 193°–194°) was added to a stirred solution of 6 ml of 2 N sodium hydroxide in 40 ml of glyme cooled to 5°. The reaction mixture was stirred for 30 min. at 5°, and then 20 ml of cold water was added. The reaction mixture was neutralized with 10% hydrochloric acid, and the precipitated solid was collected on a filter, washed with water, dried in air, and recrystallized from benzene to give 1.69 g (88%) of 8-chloro-3-fluoro-1,3-dihydro-1-methyl-6-phenyl-2H-4,1,5-benzoxadiazocin-2-one as large colorless crystals: mp 218°–220°; $^{19}F$ nmr (DMSO-d$_6$) δ −132.4 ppm (d, J=52 Hz); $^1H$ nmr (DMSO-d$_6$) δ 3.23 ppm (s), 6.22 ppm (d, J=52 Hz, 1H), and 7.64 ppm (m, 8H); $^{13}C$ nmr (DMSO-d$_6$)-partial-, δ 38.7ppm (N-CH$_3$), 163 ppm (d, $J_{CF}$=32.4 Hz, C=O), 104.2 ppm (d, $J_{CF}$=234 Hz, CHF) and 171.0 ppm (C=N, $J_{CF}$<0.5 Hz).

Anal. Calcd for C$_{16}$H$_{12}$ClFN$_2$O$_2$: C, 60.29; H, 3.79; F, 5.96; N, 8.79. Found: C, 60.48; H, 4.04; F, 6.00; N, 8.66.

Mass spec. molecular wt.: Calcd for C$_{16}$H$_{12}$N$_2$O$_2$ClF: 318.0571. Found: 318.0585.

EXAMPLE 5

7-Chloro-3-fluoro-1,3-dihydro-1-methyl-5-phenyl-2H-1,4-benzodiazepin-2-one 4-Oxide

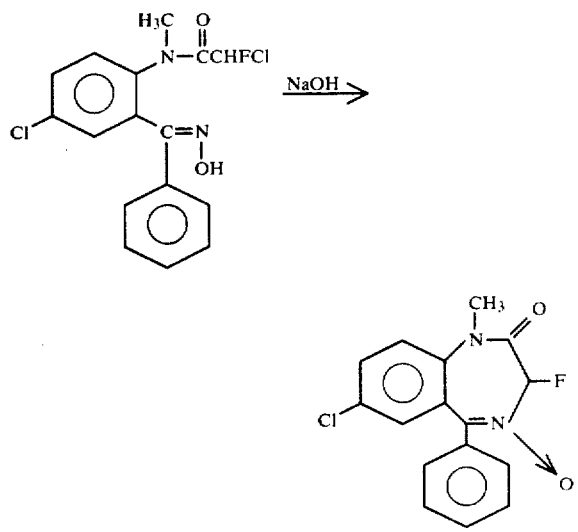

A vigorously stirred solution of 81.7 g (0.23 mole) of 5-chloro-2-(N-methyl-N-chlorofluoroacetamido)benzophenone anti-oxime in 1300 ml methylene chloride containing 500 ml of water was cooled to 5°, and 230 ml of 1 N sodium hydroxide was added dropwise over a period of 15 min. The reaction mixture was stirred for 2 hr at 5°, and then filtered to remove a small amount of suspended solid. The organic layer was separated, and the aqueous layer was extracted with 200 ml of methylene chloride. The organic layer and extract were combined, dried over 50 g of magnesium sulfate, and then evaporated to dryness under reduced pressure. The residue was suspended in 100 ml of ethanol, and then collected on a filter and washed with 100 ml of ethanol to give 62.25 g (85% yield) of 7-chloro-3-fluoro-1,3-dihydro-1-methyl-5-phenyl-2H-1,4-benzodiazepin-2-one 4-oxide as a white crystalline powder: mp 190°–192° (dec.); $^{19}F$ nmr (DMSO-d$_6$) δ −176.8 ppm (d, J=45.5 Hz); $^1H$ nmr (DMSO-d$_6$) δ 3.48 ppm (s, 3H), 6.39 ppm (d, J=45.5 Hz, 1H), 7.08 ppm (m, 1H) and 7.6 ppm (m, 7H).

Anal. Calcd for C$_{16}$H$_{12}$ClFN$_2$O$_2$: C, 60.29; ˙, 3.79; N, 8.79; F, 5.96. Found: C, 59.92; H, 4.02; N 8.63; F, 5.79.

EXAMPLE 6

7-Chloro-3-fluoro-1,3-dihydro-1-methyl-5-phenyl-2H-1,4-benzodiazepin-2-one 4-Oxide

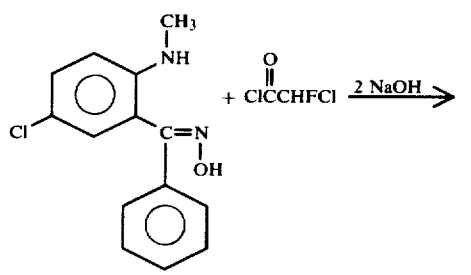

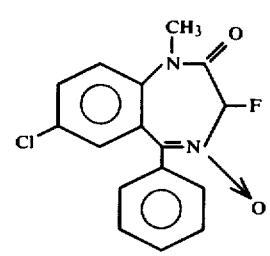

A rapidly stirred solution of 7.82 g (0.03 mole) of 5-chloro-2-methylamino anti-oxime in 100 ml of methylene chloride was mixed with 40 ml of water and cooled to 5°, and (A) 36 ml of 1 N sodium hydroxide and (B) 4.32 g (0.033 mole) of chlorofluoroacetyl chloride made up to 36 ml with methylene chloride were added at the same rate over 15 min. from separate dropping funnels. The mixture was stirred for 1 hr at 5°, and then 30 ml of 1 N sodium hydroxide was added over 15 min. The reaction mixture was stirred for an additional hr, and then neutralized with 1 N hydrochloric acid. The organic layer was separated, washed with water, dried over magnesium sulfate, and evaporated to dryness under reduced pressure. The residue was suspended in 50 ml of hot ethanol, and then cooled, collected on a filter, washed with ethanol, and dried in air to give 5.28 g (61%) of 7-chloro-3-fluoro-1,3-dihydro-1-methyl-5-phenyl-2H-1,4-benzodiazepin-2-one 4-oxide as a white crystalline powder, m.p. 177°-79° C.

EXAMPLE 7

7-Chloro-3-fluoro-1.3-dihydro-1-methyl-5-phenyl-2H-1,4-benzodiazepin-2-one 4-Oxide

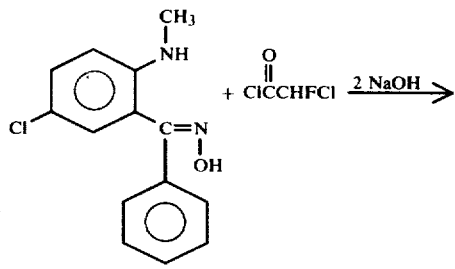

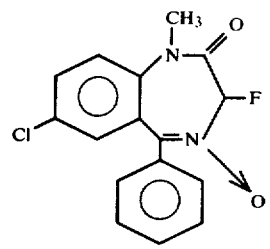

A stirred solution of 7.82 g (0.03 mole) of 5-chloro-2-methylamino anti-oxime in 100 ml of toluene was mixed with 40 ml of water and cooled to 5°, and (A) 4.32 g (0.033 mole) of chlorofluoroacetyl chloride made up to 36 ml with toluene and (B) 36 ml of 1 N sodium hydroxide were added at the same rate over 15 min. The reaction mixture was stirred for 5 hr at 5°, and the solid that precipitated was collected on a filter, washed with water and then alcohol to give 4.48 g of 7-chloro-3-fluoro-1,3-dihydro-1-methyl-5-phenyl-2H-1,4-benzodiazepin-2-one 4-oxide as a white crystalline powder, m.p. 189°-191° (dec.).

EXAMPLE 8

Part A,
2-(Chlorofluoroacetamido)-5-chlorobenzophenone Oxime (Mixture of Isomers)

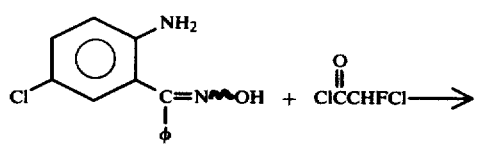

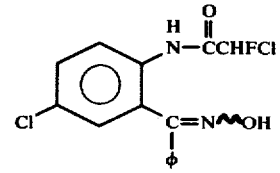

Water, 250 ml, was added to a solution of 50 g (0.203 mole) of 2-amino-5-chlorobenzophenone oxime (mixture of isomers) in 1 l. of ether, and the mixture was stirred rapidly and cooled to 5°. Solutions of (A) 100 ml of 10% sodium hydroxide in water and (B) 33.5 g (0.228 mole) of chlorofluoroacetyl chloride made up to 100 ml with ether were simultaneously added at the same rate over 30 min., keeping the temperature of the reaction mixture at about 10° with cooling. The reaction mixture was stirred for 30 min. after the addition, and the ether layer was separated, washed with water, dried (MgSO$_4$), and evaporated to dryness under reduced pressure. The residue was recrystallized from benzene to give 61.2 g (88%) of 2-(chlorofluoroacetamido)-5-chlorobenzophenone oxime (mixture of isomers) as light yellow crystals, mp 110°-129°. The $^{19}$F nmr (acetone-d$_6$) indicates a mixture of two isomers in a 70:30 ratio: δ −143.2 ppm (d, d, J=50, 2.5 Hz, 30%) and δ −144.3 ppm (d, d, J=50, 2.5 Hz, 70%).

Part B,
6-Chloro-2-chlorofluoromethyl-4-phenylquinazoline 3-Oxide

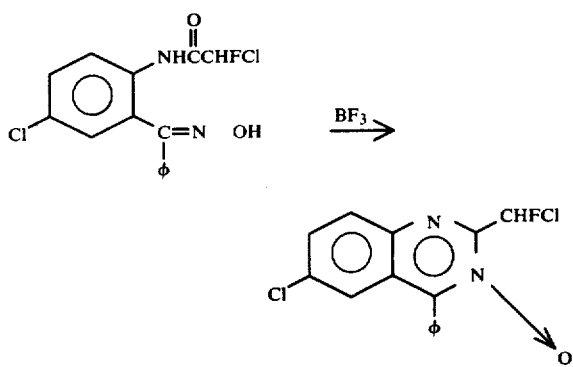

Boron trifluoride etherate, 30 ml, was added dropwise to a solution of 58 g (0.17 mole) of 2-(chlorofluoroacetamido)-5-chlorobenzophenone oxime (mixture of isomers) in 1 l. of benzene at 50°. The reaction mixture was refluxed for 18 hr, and then cooled and stirred with 500 ml of water for 20 min. The organic layer was separated, washed with 5% aqueous sodium bicarbonate, dried (MgSO$_4$), and evaporated to dryness. The yellow residue was recrystallized from methanol to give 29 g (53%) of 6-chloro-2-chlorofluoromethyl-4-phenylquinazoline 3-oxide as light yellow crystals: mp 169°–171°; $^{19}$F nmr (DMSO-d$_6$) δ 145.1 ppm (d, J=48 Hz).

| Anal. Calcd for C$_{15}$H$_9$Cl$_2$FN$_2$O: | C, 55.75 | H, 2.81; | F, 5.88; |
|---|---|---|---|
| | N, 8.67 | | |
| Found: | C, 55.75; | H, 3.03; | F, 5.62; |
| | 55.46 | 2.84 | |
| | N, 8.72 | | |
| | 8.46 | | |

Part C,
7-Chloro-3-fluoro-1,3-dihydro-5-phenyl-2H-1,4-benzodiazepin-2-one 4-Oxide

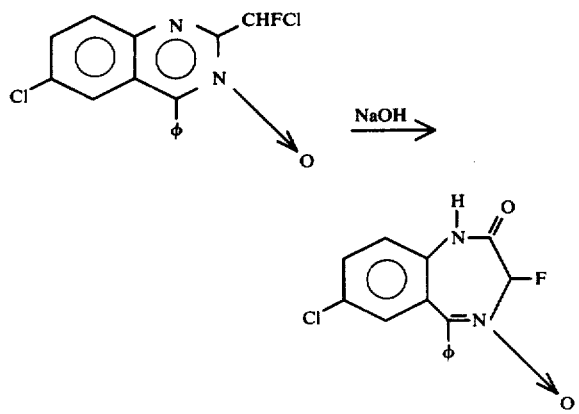

A solution of 53 ml (0.106 mole) of 2 N sodium hydroxide in 350 ml glyme was cooled to 5°, and 16.67 g (0.0516 mole) of 6-chloro-2-chlorofluoromethyl-4-phenylquinazoline 3-oxide was added portionwise over 10 min. The reaction mixture was stirred for 30 min. at 5°, and then diluted with 200 ml of cold water. The reaction mixture was neutralized with 3 N-hydrochloric acid and then poured into 1 l. of ice water. The solid that precipitated after standing for 2 hr was collected on a filter, washed with water, and dried in vacuum over P$_2$O$_5$. There was obtained 14.7 g (93%) of 7-chloro-3-fluoro-1,3-dihydro-5-phenyl-2H-1,4-benzodiazepin-2-one 4-oxide as white crystals: mp 207°–208° (dec.); $^{19}$F nmr (DMSO-d$_6$) δ −179.5 ppm (d, J=46 Hz); $^1$H nmr (DMSO-d$_6$) δ 6.33 ppm (d, J=46 Hz, 1H), 7.04 ppm (d, J=2 Hz, 1H) and 7.52 ppm (m, 7H); ir (KBr) 5.78μ (C=O) and 8.45μ (N→O).

Anal. Calcd for C$_{15}$H$_{10}$ClFN$_2$O$_2$: C, 59.13; H, 3.31; F, 6.23; N, 9.19. Found: C, 58.94; H, 3.50; F, 5.95; N, 9.00.

Part D,
7-Chloro-3-fluoro-1,3-dihydro-1-methyl-5-phenyl-2H-1,4-benzodiazepin-2-one 4-Oxide

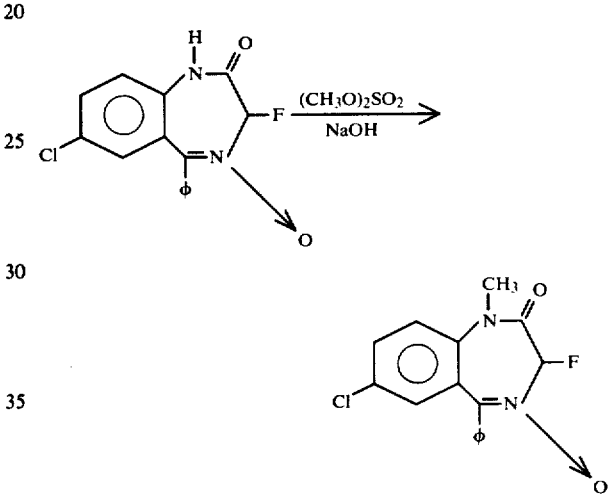

Methyl sulfate, 2.2 ml (0.023 mole) was added dropwise to a stirred suspension of 6.1 g (0.02 mole) of 7-chloro-3-fluoro-1,3-dihydro-5-phenyl-2H-1,4-benzodiazepin-2-one 4-oxide in a cooled solution prepared by dissolving 1.0 g (0.025 mole) of sodium hydroxide in 170 ml water and 34 ml ethanol. The reaction mixture was stirred at 10° for 4 hr. The solid that precipitated was collected on a filter, washed with water, and dried in vacuum over phosphorous pentoxide to give 4.1 g (64%) of product as a white crystalline powder. Recrystallization from methyl ethyl ketone gave a 1:1 solvate: mp 95°–97°, resolidified and then melted with decomposition at 167°–169°; $^{19}$F nmr (DMSO-d$_6$) δ −176.7 ppm (d, J=46 Hz).

Anal. Calcd for C$_{16}$H$_{12}$ClFN$_2$O$_2$·C$_4$H$_8$O: C, 61.46; H, 5.16; N, 7.17. Found: C, 61.56; H, 5.03; N, 6.88.

Pure 7-chloro-3-fluoro-1,3-dihydro-1-methyl-5-phenyl-2H-1,4-benzodiazepin-2-one 4-oxide was obtained by heating 2.04 g of the solvate in vacuum (0.5 mm) at 100° for 4 hr to give 1.67 g of a white crystalline powder: mp 167°–169° (dec.); $^{19}$F nmr (DMSO-d$_6$) δ −176.9 ppm (d, J=45 Hz); $^1$H nmr (DMSO-d$_6$) δ 3.48 ppm (s, 3H), 6.39 ppm (d, J=45 Hz, 1H), 7.08 ppm (m, 1H) and 7.6 ppm (m, 7H); ir (KBr) 5.83μ (C=O), 8.40μ (N→O).

Anal. Calcd for C$_{16}$H$_{12}$ClFN$_2$O$_2$: C, 60.29; H, 3.79; F, 5.96; N, 8.79. Found: C, 60.11; H, 3.79; F, 5.46; N, 8.69.

EXAMPLE 9

7-Chloro-3-fluoro-1,3-dihydro-1-methyl-5-phenyl-2H-1,4-benzodiazepin-2-one

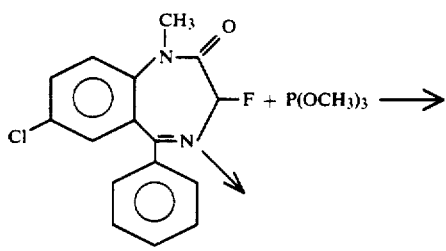

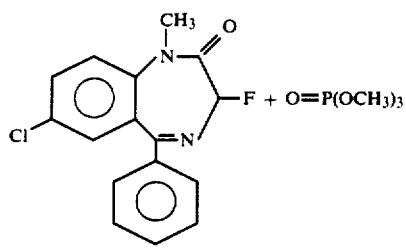

A solution of 15.93 g (0.05 mole) of 7-chloro-3-fluoro-1,3-dihydro-1-methyl-5-phenyl-2H-1,4-benzodiazepin-2-one 4-oxide and 20 ml (0.16 mole) of trimethyl phosphite in 250 ml of methylene chloride was allowed to remain at room temperature (about 25° C.) for 3 days, and then evaporated to dryness under reduced pressure. The residue was suspended in water, collected on a filter, washed thoroughly with water, and dried in air to give 14.91 g (98.5% yield) of crude 7-chloro-3-fluoro-1,3-dihydro-1-methyl-5-phenyl-2H-1,4-benzodiazepin-2-one as a white powder. Analysis by high pressure liquid chromatography indicated the product was 98.9% pure. Recrystallization from ethanol gave colorless crystals: mp 145°-147°; $^{19}F$ nmr (CDCl$_3$) δ −161.7 ppm (d, J=57 Hz); $^{1}H$ nmr (CDCl$_3$) δ 3.43 ppm (s, 3H), 5.54 ppm (d, J=57 Hz, 1H) and 7.5 ppm (m, 8H).

Anal. Calcd for C$_{16}$H$_{12}$ClFN$_2$O: C, 63.47; H, 4.00; F, 6.28; N, 9.26. Found: C, 63.77; H, 4.31; F, 6.32; N, 9.31.

EXAMPLE 10

7-Chloro-3-fluoro-1,3-dihydro-1-methyl-5-phenyl-2H-1,4-benzodiazepin-2-one

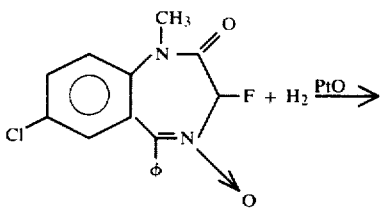

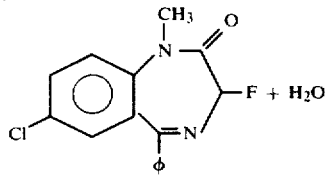

A solution of 0.5 g of 7-chloro-3-fluoro-1,3-dihydro-1-methyl-5-phenyl-2H-1,4-benzodiazepin-2-one 4-oxide in 50 ml of tetrahydrofuran containing 0.2 g of platinum oxide was shaken under 40 lb/in$^2$ of hydrogen pressure for 2 hr. The catalyst was filtered off, and the filtrate was evaporated to dryness under reduced pressure to give 0.47 g of a light yellow residue. $^{1}H$ and $^{19}F$ nmr analysis indicated that the product was 73% 7-chloro-3-fluoro-1,3-dihydro-1-methyl-5-phenyl-2H-1,4-benzodiazepin-2-one, $^{19}F$ nmr (CDCl$_3$) δ −161.7 ppm (d, J=57 Hz$_2$).

EXAMPLE 11

7-Chloro-3-fluoro-1,3-dihydro-1-methyl-5-phenyl-2H-1,4-benzodiazepin-2-one

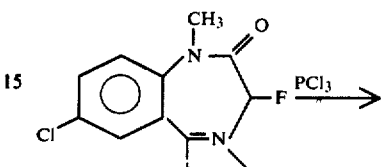

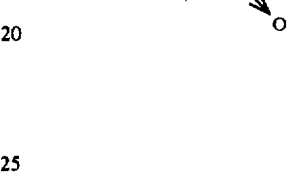 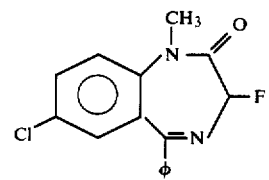

A 580 μl (6.6 mmole) of phosphorous trichloride was added to a solution of 1.05 g (3.3 mmole) of 7-chloro-3-fluoro-1,3-dihydro-1-methyl-5-phenyl-2H-1,4-benzodiazepin-2-one 4-oxide in 15 ml methylene chloride at 5°. The solution was stirred for 2 hr at 5° and then 20 hr at 25°, and then poured into 100 ml of cold aqueous 5% sodium bicarbonate solution. The organic layer was separated, washed with water, dried (MgSO$_4$) and evaporated to dryness to give 800 mg (80%) of crude product. Recrystallization from heptane gave 650 mg (65%) of 7-chloro-3-fluoro-1.3-dihydro-1-methyl-5-phenyl-2H-1,4-benzodiazepin-2-one as colorless crystals, mp 139°-140°. Even under these mild conditions, an appreciable amount of 3,7-dichloro-1,3-dihydro-1-methyl-5-phenyl-2H-1,4-benzodiazepin-2-one is formed as an impurity. If the reaction mixture is heated to 61° C. for only 10 min., none of the desired 3-fluoro compound is formed.

Synthesis of the fluorohaloacetyl halide starting material

The following example illustrates preparation of the fluorohaloacetyl halide starting material. Parts are by weight and temperature is in degrees Centigrate unless otherwise stated.

EXAMPLE 12

A. Sodium Chlorofluoroacetate

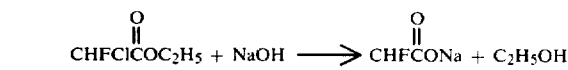

Eight hundred ml (4 mole) of 5 N sodium hydroxide was added dropwise over a period of 30 min. to a stirred sample of 523.8 g (4.0 mole) of ethyl chlorofluoroacetate (prepared as described by B. Englund, "Organic Syntheses," Col. Vol. IV, p. 184, John Wiley and Sons, Inc., New York, 1963) contained in a 1-liter flask cooled in an ice bath. Stirring was continued until a homogenous solution was obtained (about 30 min.), and then the resulting solution was evaporated to dryness at 100° and under reduced pressure. The white residue was broken up and dried in a vacuum oven at 80° to give 504 g (94%) of sodium chlorofluoroacetate as a white crystalline powder.

Part B. Chlorofluoroacetyl Chloride

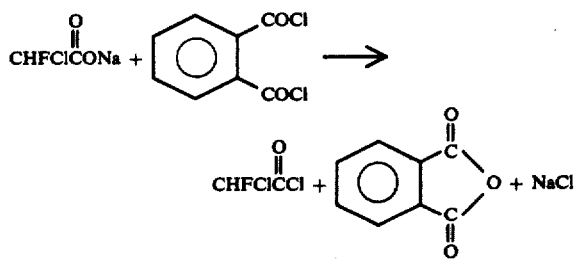

A 3-l., three-necked flask was fitted with a thermometer, a heating mantle, a mechanical stirrer, and a distillation head with a condenser and a 500 ml receiving flask backed up by a dry ice cooled trap. The reaction flask was charged with 500 g (3.72 mole) of crude sodium chlorofluoroacetate and 1 l. (1400 g. 6.9 mole) of practical grade phthaloyl chloride. The stirrer was started, and the contents of the flask were heated slowly until product began to distill from the reaction mixture (pot temperature about 100°-110°). The heating mantle was turned off until the initial reaction subsided, and then heating was resumed and continued until the pot temperature reached 245°. The distillate in the receiver and the dry ice cooled trap were combined (437 g. 90% crude yield) and redistilled through an 18 in. spinning band column to give 330.8 g (68%) of chlorofluoroacetyl chloride as a colorless liquid, bp 69°-69.5°. The fraction boiling between 65° and 69° was redistilled to give an additional 45.3 g (9.3%), which is a total yield of 376.1 g (77%) of product boiling at 69°-69.5°.

Table I shows additional fluorohaloacetamidobenzophenone anti-oximes that can be made by the process disclosed and exemplified above using the appropriate anti-oxime of formula I and an appropriate fluorohaloacetyl halide.

TABLE I

Preparation of 3-Fluorohaloacetamidobenzophenone anti-Oximes

| Reactants | | |
|---|---|---|
| Oxime | Fluorohaloacetyl Halide | Product |
| [structure: 4-Br, 2-(CH3NH), benzophenone oxime] | + CHFCl—CBr(=O) → | [structure: 4-Br, 2-(N(CH3)—C(=O)CHFCl), benzophenone oxime] |
| [structure: 4-O2N, 2-(CH3NH), benzophenone oxime] | + CHFBrCOCl → | [structure: 4-O2N, 2-(N(CH3)—C(=O)CHFBr), benzophenone oxime] |
| [structure: 4-CF3, 2-(CH3NH), benzophenone oxime] | + CHFClCOCl → | [structure: 4-CF3, 2-(N(CH3)—C(=O)CHFCl), benzophenone oxime] |

TABLE I-continued
Preparation of 3-Fluorohaloacetamidobenzophenone anti-Oximes

| Oxime | Fluorohaloacetyl Halide | Product |
|---|---|---|
| (5-Br, 2-NHCH₃ benzophenone with 2'-F, oxime) | + CHFClCCl (with =O) | (N(CH₃)COCHFCl amide analog) |
| (5-Cl, 2-NHCH₃ benzophenone with 2'-Cl, oxime) | + CHFClCCl (with =O) | (N(CH₃)COCHFCl amide analog) |

Table II shows additional 3-fluorobenzodiazepin 4-oxides that can be made by the processes disclosed and exemplified above using the appropriate anti-oxime of formula II and a suitable base.

TABLE II
Preparation of 3-Fluorobenzodiazepin 4-Oxides

| anti-Oxime | Base | Product |
|---|---|---|
| (5-Br, N-CH₃, N-COCHFCl amidobenzophenone oxime) | + KOH | (7-Br, 1-methyl-3-fluoro-5-phenyl-benzodiazepin-2-one 4-oxide) |
| (5-NO₂, N-CH₃, N-COCHFBr amidobenzophenone oxime) | + NaOH | (7-NO₂, 1-methyl-3-fluoro-5-phenyl-benzodiazepin-2-one 4-oxide) |

TABLE II-continued
Preparation of 3-Fluorobenzodiazepin 4-Oxides

| Reactants | | Product |
|---|---|---|
| anti-Oxime | Base | |
| [structure: 4-CF₃ phenyl with N(CH₃)-C(O)-CCHFCl and C(=NOH)-phenyl] | + KOH ⟶ | [structure: 7-CF₃ 1-methyl 3-fluoro 5-phenyl benzodiazepine 4-oxide] |
| [structure: 4-Br phenyl with N(CH₃)-C(O)-CCHFCl and C(=NOH)-(2-F-phenyl)] | + NaOH ⟶ | [structure: 7-Br 1-methyl 3-fluoro 5-(2-fluorophenyl) benzodiazepine 4-oxide] |
| [structure: 4-Cl phenyl with N(CH₃)-C(O)-CCHFCl and C(=NOH)-(2-Cl-phenyl)] | + KOH ⟶ | [structure: 7-Cl 1-methyl 3-fluoro 5-(2-chlorophenyl) benzodiazepine 4-oxide] |

Table III shows additional 3-fluorobenzodiazepines that can be prepared by the processes disclosed and exemplified above using an appropriate N-oxide and a suitable reducing agent.

TABLE III
Preparation of 3-Fluorobenzodiazepines

| Reactants | | Product |
|---|---|---|
| Oxide | Reducing Agent | |
| [structure: 7-Br 1-methyl 3-fluoro 5-phenyl benzodiazepine 4-oxide] | + P(OCH₃)₃ ⟶ | [structure: 7-Br 1-methyl 3-fluoro 5-phenyl benzodiazepine] |
| [structure: 7-O₂N 1-methyl 3-fluoro 5-phenyl benzodiazepine 4-oxide] | + P(C₆H₅)₃ ⟶ | [structure: 7-O₂N 1-methyl 3-fluoro 5-phenyl benzodiazepine] |

TABLE III-continued
Preparation of 3-Fluorobenzodiazepines

| Reactants | | Product |
|---|---|---|
| Oxide | Reducing Agent | |

[Chemical structures: Row 1 — 7-trifluoromethyl-1-methyl-3-fluoro-5-phenyl-benzodiazepine 4-oxide + P(OC$_2$H$_5$)$_3$ → corresponding benzodiazepine; Row 2 — 7-bromo-1-methyl-3-fluoro-5-(2-fluorophenyl)-benzodiazepine 4-oxide + PCl$_2$OCH$_3$ → corresponding benzodiazepine; Row 3 — 7-chloro-1-methyl-3-fluoro-5-(2-chlorophenyl)-benzodiazepine 4-oxide + P(OCH$_3$)$_3$ → corresponding benzodiazepine]

Dosage Forms

The tranquilizers, muscle relaxants, and sedatives of formulae II and III can be administered to produce the desired effect by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.05 to 500 milligrams per kilogram of body weight. Ordinarily 0.5 to 50, and preferably 1.0 to 25 milligrams per kilogram per day given in divided doses 2 to 4 times a day or in sustained release form is effective to obtain desired results.

In pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 20.0 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 10 milligram of the active ingredient. The capsules are washed in petroleum ether and dried.

Tablets

A large number of tablets are prepared by conventional procedures so that the dosage unit is 5.0 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 5.0 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

Utility

Standard procedures for detecting and comparing the tranquilizer, muscle-relaxant, and sedative activity of compounds in this series for which there is a correlation with human efficacy are the following: pinna reflex tests, prehensile traction reflex tests, a muscle relaxant (anti-Straub tail) test, an antipentylenetetrazole test, and a mouse activity supression test (MAST).

PINNA REFLEX TESTS

Fasted female white mice, 5 per dose are intubated with drug at 4, 12, 36, 108 and 324 mg/kg in 1% Methocel®-1.25% Tween 80®, at 10 ml/kg. The auditory and tactile pinna are tested at 0.5, 2, 5 and 24 hours.

Auditory Pinna Reflex

The mouse is placed on a horizontal bar 9 cm from a Galton whistle adjusted for 13 Kc. Failure to flatten the ears during one or two short bursts of sound constitutes loss of auditory pinna reflex.

Tactile Pinna Reflex

The mouse is held by the tail and the hairs inside the right ear are touched by the fine wire stylus from a 27 gauge needle. Failure of the mouse to twitch or move the head constitutes loss of the tactile pinna reflex.

PREHENSILE TRACTION TESTS

Grip and Lift Reflexes

The mouse is gently swung by the tail toward a horizontal 12 gauge wire tautly stretched 25 cm above the bench. After the mouse grasps the wire with its forepaws, its posterior end is held directly below the wire. A normal mouse grasps the wire with its forepaws and immediately lifts its hind limbs to the wire. Failure to grasp the wire with the forepaws in one of 2 trials constitutes loss of the grip reflex; failure to lift the hind limbs to grasps the wire with at least one hind paw within 5 seconds constitutes loss of the lift reflex.

MUSCLE RELAXANT (ANTI-STRAUB TAIL) TEST

Fasted female white mice, 5 per dose are intubated with test drug. Twenty-five minutes later morphine sulfate is given subcutaneously at 53.7 mg/kg. Thirty minutes after test drug the mice are observed for presence of Straub tail. Quantal ED50 values for blockade of morphine-induced Straub tail are calculated.

ANTIPENTYLENETETRAZOLE (PTZ) TEST

Fasted female white mice, 10 per dose are intubated with drug in vehicle as above at doses such as 0, 1, 3, 9, 27 and 81 mg/kg. Thirty minutes later the mice are dosed intravenously with PTZ (Metrazol®[1]) at 40 mg/kg (ED98 for clonic convulsions). Dosed animals which remain on a 4"×4" platform for 20 seconds are considered protected. Quantal ED50's are calculated by the moving average method.

[1]Original brand of pentylenetetrazole; sterile 10% aqueous solution for parenteral injection, Knoll Pharmaceutical Company.

MOUSE ACTIVITY SUPPRESSION TEST (MAST)

The mouse activity suppression test (MAST) is a model system designed to detect compounds with possible antianxiety activity in humans. The test is based upon punishment of mice for exhibiting normal exploratory locamotor behavior. The punishment, an electric shock applied through the mouse's paws, quickly extinguishes normal behavior. Pretreatment with a minor tranquilizer prevents or delays the extinction, while major tranquilizers, analgesics, stimulants, antidepressants, antihistaminics, and purely sedative drugs are inactive.

The test procedure is modified from Boissier, et al., European J. Pharm., 4, 145-151 (1968). Female white mice, fasted 16–22 hours, are randomly distributed to fiberglass holding boxes. Mice in groups of 10–20 are dosed orally and returned to their holding boxes until test time. Test drug suspensions or solutions are prepared by sonication in 1% Methocel®. Typical dose ranges include 0.5, 1, 2, and 4 mg/kg of 1, 3 9, 27, 81 mg/kg plus a vehicle control and are selected to include one dose at which an effect such as sedation, stimulation, muscle weakness or analgesia was seen.

The test apparatus is an opaque, black plastic box with a clear lid and a stainless steel grid floor. The floor of the test box is marked off into four squares of equal size.

After dosing, a mouse is gently placed in one corner of the testing box and during the next minute each time the mouse makes a full crossing from one square section of the box to another the floor is electrified with 0.2 ma current for 2.0 seconds.

The number of shocks received by each mouse is recorded and the mean number of shocks/dose ($\bar{X}$) is determined. When $\bar{X}$ drug at any dose is statistically greater than $\bar{X}$ controls (Kruskal-Wallis test in S. Siegel[1]), antagonism of suppression obtains and the drug is presumed to have antianxiety activity.

[1] S. Siegel: Non-parametric Statistics for Behavioral Sciences, pp. 184–194, McGraw-Hill (1956).

Potency in the antipentylenetetrazole (PTZ) and the MAST indicates a potent antianxiety agent. Great potency for blockade of the mouse auditory pinna reflex with little or no effect on tactile pinna reflex is characteristic of minor tranquilizers. Centrally acting skeletal muscle relaxants profoundly affect the lift reflex with little effect on the grip reflex. Potency in the mouse anti-Straub tail test suggests skeletal muscle relaxant activity.

The following table includes the results of these tests conducted with the compounds of this invention; it also includes the results for diazepam and chlordiazepoxide, two well-known benzodiazepines widely-used commercially as tranquilizers.

TABLE 4

| Compound | Mouse ED50 values | | | | | | |
| | Pinna Reflexes | | Prehensile Reflexes | | Muscle | | Mast |
| | Auditory | Tactile | Lift | Grip | Relaxant | PTZ | ED20% |
| (I) | 23. | 360. | 36. | 70. | 5.8 | 4.5 | 3.5 |
| (II) | 62. | >450. | 62. | >450. | 1.7 | 3.9 | 0.35 |
| Chlordiazepoxide | 17. | 209. | 11. | 232. | 1.9 | 4.5 | 1.9 |
| Diazepam | 4. | 109. | 6. | 97. | 0.25 | 1.3 | 0.45 |

(I) = 5-chloro-2-(N-methyl-N-chlorofluoroacetamide)-benzophenone anti-oxime (II) = 7-chloro-3-fluoro-1,3-dihydro-1-methyl-5-phenyl-2H-1,4-benzodiazepin-2-one 4-oxide.

I claim:
1. A compound of the formula:

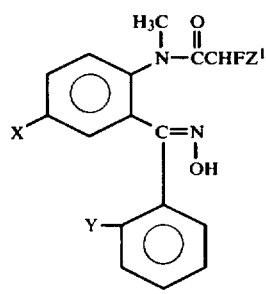

where
X is Cl, Br, NO$_2$, or CF$_3$;
Y is H, Br, Cl, or F; and
Z$^1$ is Cl or Br.

2. A compound of claim 1 where X is chlorine or bromine.

3. A compound of claim 1 where Y is hydrogen, chlorine or fluorine.

4. A compound of claim 2 where Y is hydrogen, chlorine or fluorine.

5. A compound of claim 2 where Y is hydrogen or fluorine.

6. The compound of claim 1 where X is chlorine, Y is hydrogen and Z$^1$ is chlorine.

7. A compound of the formula:

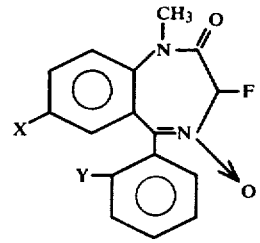

where
X is Cl, Br, NO$_2$ or CF$_3$; and
Y is H, Br, Cl or F.

8. A compound of claim 7 where X is chlorine or bromine.

9. A compound of claim 7 where Y is hydrogen, chlorine or fluorine.

10. A compound of claim 8 where Y is hydrogen, chlorine or fluorine.

11. A compound of claim 8 where Y is hydrogen or fluorine.

12. The compound of claim 7 where X is chlorine and Y is hydrogen.

13. A pharmaceutical composition comprising a pharmaceutically suitable carrier and an effective tranquilizing amount of a compound of claim 1.

14. A pharmaceutical composition comprising a pharmaceutically suitable carrier and an effective tranquilizing amount of a compound of claim 2.

15. A pharmaceutical composition comprising a pharmaceutically suitable carrier and an effective tranquilizing amount of a compound of claim 3.

16. A pharmaceutical composition comprising a pharmaceutically suitable carrier and an effective tranquilizing amount of a compound of claim 4.

17. A pharmaceutical composition comprising a pharmaceutically suitable carrier and an effective tranquilizing amount of a compound of claim 5.

18. A pharmaceutical composition comprising a pharmaceutically suitable carrier and an effective tranquilizing amount of a compound of claim 6.

19. A pharmaceutical composition comprising a pharmaceutically suitable carrier and an effective tranquilizing amount of a compound of claim 7.

20. A pharmaceutical composition comprising a pharmaceutically suitable carrier and an effective tranquilizing amount of a compound of claim 8.

21. A pharmaceutical composition comprising a pharmaceutically suitable carrier and an effective tranquilizing amount of a compound of claim 9.

22. A pharmaceutical composition comprising a pharmaceutically suitable carrier and an effective tranquilizing amount of a compound of claim 10.

23. A pharmaceutical composition comprising a pharmaceutically suitable carrier and an effective tranquilizing amount of a compound of claim 11.

24. A pharmaceutical composition comprising a pharmaceutically suitable carrier and an effective tranquilizing amount of a compound of claim 12.

25. A method of tranquilizing a mammal which comprises administering to the mammal an effective tranquilizing amount of a compound of claim 1 at a daily dosage rate of 0.05 to 500 mg/kg of body weight.

26. A method of tranquilizing a mammal which comprises administering to the mammal an effective tranquilizing amount of a compound of claim 2 at a daily dosage rate of 0.05 to 500 mg/kg of body weight.

27. A method of tranquilizing a mammal which comprises administering to the mammal an effective tranquilizing amount of a compound of claim 3 at a daily dosage rate of 0.05 to 500 mg/kg of body weight.

28. A method of tranquilizing a mammal which comprises administering to the mammal an effective tranquilizing amount of a compound of claim 4 at a daily dosage rate of 0.05 to 500 mg/kg of body weight.

29. A method of tranquilizing a mammal which comprises administering to the mammal an effective tranquilizing amount of a compound of claim 5 at a daily dosage rate of 0.05 to 500 mg/kg of body weight.

30. A method of tranquilizing a mammal which comprises administering to the mammal an effective tranquilizing amount of a compound of claim 6 at a daily dosage rate of 0.05 to 500 mg/kg of body weight.

31. A method of tranquilizing a mammal which comprises administering to the mammal an effective tranquilizing amount of a compound of claim 7 at a daily dosage rate of 0.05 to 500 mg/kg of body weight.

32. A method of tranquilizing a mammal which comprises administering to the mammal an effective tranquilizing amount of a compound of claim 8 at a daily dosage rate of 0.05 to 500 mg/kg of body weight.

33. A method of tranquilizing a mammal which comprises administering to the mammal an effective tranquilizing amount of a compound of claim 9 at a daily dosage rate of 0.05 to 500 mg/kg of body weight.

34. A method of tranquilizing a mammal which comprises administering to the mammal an effective tranquilizing amount of a compound of claim 10 at a daily dosage rate of 0.05 to 500 mg/kg of body weight.

35. A method of tranquilizing a mammal which comprises administering to the mammal an effective tranquilizing amount of a compound of claim 11 at a daily dosage rate of 0.05 to 500 mg/kg of body weight.

36. A method of tranquilizing a mammal which comprises administering to the mammal an effective tranquilizing amount of a compound of claim 12 at a daily dosage rate of 0.05 to 500 mg/kg of body weight.

* * * * *